US009579368B2

(12) United States Patent
Bratbak et al.

(10) Patent No.: US 9,579,368 B2
(45) Date of Patent: Feb. 28, 2017

(54) TREATMENT OF HEADACHE BY INJECTION OF NEUROINHIBITORY SUBSTANCE TO SPHENOPALATINE GANGLION OR OTIC GANGLION

(71) Applicant: NORWEGIAN UNIVERSITY OF SCIENCE AND TECHNOLOGY (NTNU), Trondheim (NO)

(72) Inventors: Daniel Fossum Bratbak, Trondheim (NO); Ståle Nordgård, Heimdal (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 0 days.

(21) Appl. No.: 14/426,303

(22) PCT Filed: Sep. 6, 2013

(86) PCT No.: PCT/EP2013/068515
§ 371 (c)(1),
(2) Date: Mar. 5, 2015

(87) PCT Pub. No.: WO2014/037531
PCT Pub. Date: Mar. 13, 2014

(65) Prior Publication Data
US 2015/0306188 A1    Oct. 29, 2015

(30) Foreign Application Priority Data

Sep. 6, 2012 (GB) .................................. 1215949.7
Sep. 6, 2012 (GB) .................................. 1215950.5

(51) Int. Cl.
| | | |
|---|---|---|
| *A61K 38/48* | (2006.01) | |
| *A61B 10/02* | (2006.01) | |
| *A61B 17/34* | (2006.01) | |
| *A61M 5/20* | (2006.01) | |
| *A61M 5/24* | (2006.01) | |
| *A61K 9/00* | (2006.01) | |
| *A61M 5/28* | (2006.01) | |
| *A61M 5/32* | (2006.01) | |
| *A61B 17/00* | (2006.01) | |

(52) U.S. Cl.
CPC ...... *A61K 38/4893* (2013.01); *A61B 10/0233* (2013.01); *A61B 17/3403* (2013.01); *A61K 9/0019* (2013.01); *A61M 5/20* (2013.01); *A61M 5/24* (2013.01); *A61M 5/28* (2013.01); *A61M 5/3286* (2013.01); *A61B 2010/0208* (2013.01); *A61B 2017/00199* (2013.01); *A61B 2034/2051* (2016.02); *A61B 2034/2055* (2016.02); *A61B 2034/2068* (2016.02); *A61B 2090/372* (2016.02); *A61B 2090/397* (2016.02); *A61B 2090/3937* (2016.02); *A61B 2090/3983* (2016.02); *A61M 2005/206* (2013.01); *A61M 2209/01* (2013.01); *A61M 2210/0687* (2013.01)

(58) Field of Classification Search
None
See application file for complete search history.

(56) References Cited

U.S. PATENT DOCUMENTS

| | | | | |
|---|---|---|---|---|
| 5,766,605 | A * | 6/1998 | Sanders | A61K 38/4893 424/236.1 |
| 6,351,659 | B1 * | 2/2002 | Vilsmeier | A61B 6/12 600/407 |
| 7,981,433 | B2 * | 7/2011 | Blumenfeld | A61K 9/0014 424/236.1 |
| 8,231,588 | B2 * | 7/2012 | Xia | A61M 11/06 604/187 |
| 8,846,622 | B2 * | 9/2014 | Blumenfeld | A61K 9/0014 424/239.1 |
| 2003/0208122 | A1 | 11/2003 | Melkent et al. | |
| 2005/0020909 | A1 | 1/2005 | Moctezuma de la Barrera et al. | |
| 2005/0154296 | A1 | 7/2005 | Lechner et al. | |
| 2005/0267009 | A1 * | 12/2005 | Deagle | A61K 38/20 514/8.4 |
| 2006/0063973 | A1 | 3/2006 | Makower et al. | |
| 2006/0171963 | A1 | 8/2006 | Blumenfeld | |
| 2007/0208252 | A1 | 9/2007 | Makower | |
| 2008/0103509 | A1 | 5/2008 | Goldbach | |
| 2008/0185430 | A1 | 8/2008 | Goldbach | |
| 2008/0279895 | A1 | 11/2008 | Blumenfeld | |

(Continued)

FOREIGN PATENT DOCUMENTS

DE    202007004191 U1    6/2007
EP         1444962 A2    8/2004

(Continued)

OTHER PUBLICATIONS

Felisati G. et al. Sphenopalatine Endoscopic Ganglion Block. The Larygoscope 116(8)1447-50, Aug. 2006.*

(Continued)

*Primary Examiner* — Ralph Gitomer
(74) *Attorney, Agent, or Firm* — Banner & Witcoff, Ltd.

(57) ABSTRACT

A neuroinhibitory substance for use in a method for treating or preventing headache comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

26 Claims, 9 Drawing Sheets

(56) References Cited

U.S. PATENT DOCUMENTS

| | | | |
|---|---|---|---|
| 2010/0030187 A1* | 2/2010 | Xia | A61M 11/00 604/514 |
| 2010/0100081 A1 | 4/2010 | Tuma et al. | |
| 2010/0227822 A1 | 9/2010 | Blumenfeld | |
| 2013/0218142 A1 | 8/2013 | Tuma et al. | |
| 2015/0265769 A1* | 9/2015 | Bratbak | A61B 10/0233 600/567 |

FOREIGN PATENT DOCUMENTS

| | | |
|---|---|---|
| EP | 1915962 A1 | 4/2008 |
| EP | 2179703 A1 | 4/2010 |
| WO | 2005000139 A1 | 1/2005 |
| WO | 2008091917 A2 | 7/2008 |
| WO | 2009107703 A1 | 9/2009 |
| WO | 2011084507 A1 | 7/2011 |

OTHER PUBLICATIONS

International Search Report and Written Opinion mailed Dec. 12, 2013 (PCT/EP2013/068508); ISA/EP.
International Search Report and Written Opinion mailed Jan. 2, 2014 (PCT/EP2013/068515); ISA/EP.
Piagkou M N et al: "The Pterygopalatine Ganglion and its Role in Various Pain Syndromes: From Anatomy to Clinical Practice", EMBASE, Jun. 1, 2012 (Jun. 1, 2012), XP002717711, the whole article.
Slades G et al: "Control of lacrimal secretion after sphenopalatine ganglion block" Ophthalmic Plastic and Reconstructive Surgery, Masson, New York, NY, US, vol. 2, No. 2, Jan. 1, 1986 (Jan. 1, 1986), pp. 65-70, XPO09174933, ISSN: 0740-9303, figure 2, abstract, rest of article.
Dec. 18, 2012 (GB) Search Report—App 1215949.7.
Dec. 18, 2012 (GB) Search Report—App 1215950.5.
Varghese et al., Endoscopic transnasal neurolytic sphenopalatine ganglion block for head and neck cancer pain, The Journal of Larygology & Otology, May 2001, vol. 115, pp. 385-387.
Olesen, The role of nitric oxide (No) in migraine, tension-type headache and cluster headache, Pharmacology & Therapeutics, 120 (2008) 157-171.
Cohen et al., Functional neuroimaging of primary headache disorders, Expert Rev. Neurotherapeutics, 6(8), (2006), 1159-1171.
Maizels et al., Intranasal Lidocaine for Migraine: A Randomized Trial and Open-Label Follow-up, Headache, 1999; 39(8):543-51.
Cassano et al., Sphenopalatine artery ligation with nerve resection in patients with vasomotor rhinitis and polyposis: a prospective, randomized, double-blind investigation, Acta Oto-Laryngologica, 2012;132(5):525-32.
Goadsby, Pathophysiology of cluster headache: a trigeminal autonomic cephalgia, Lancet Neurology, 2002;1:251-57.
Goadsby et al., Trigeminal automomic cephalagias: diagnostic and therapeutic developments, Current Opinion in Neurology, 2008;21:323-330.
Maizels et al., Intranasal lidocaine for treatment of migraine: a randomized, double-blind, controlled trial, JAMA, 1996;276(4):319-21.
Su et al., Antegrade transsphenoidal vidian neurectomy: Short-term surgical outcome analysis, American Journal of Rhinology & Allergy, 2011;25:e217-e220.
Yang et al., A novel approach to transnasal sphenopalatine ganglion injection, MEDLINE abstract Accession No. NLM16703973, Pain Physician, vol. 9, No. 2, 2006, pp. 131-134.
Turk et al., Botulinum toxin and intractable trigeminal neuralgia, Clinical Neuropharmacology, vol. 28, No. 4, 2005, pp. 161-162.
Miles Day, Sphenopalatine ganglion analgesia, Current Review of Pain, vol. 3, No. 5, Oct. 1, 1999 (Oct. 1, 1999), pp. 342-347, XP055287005, US, ISSN: 1069-5850, DOI: 10.1007/s11916-999-0029-6.

* cited by examiner

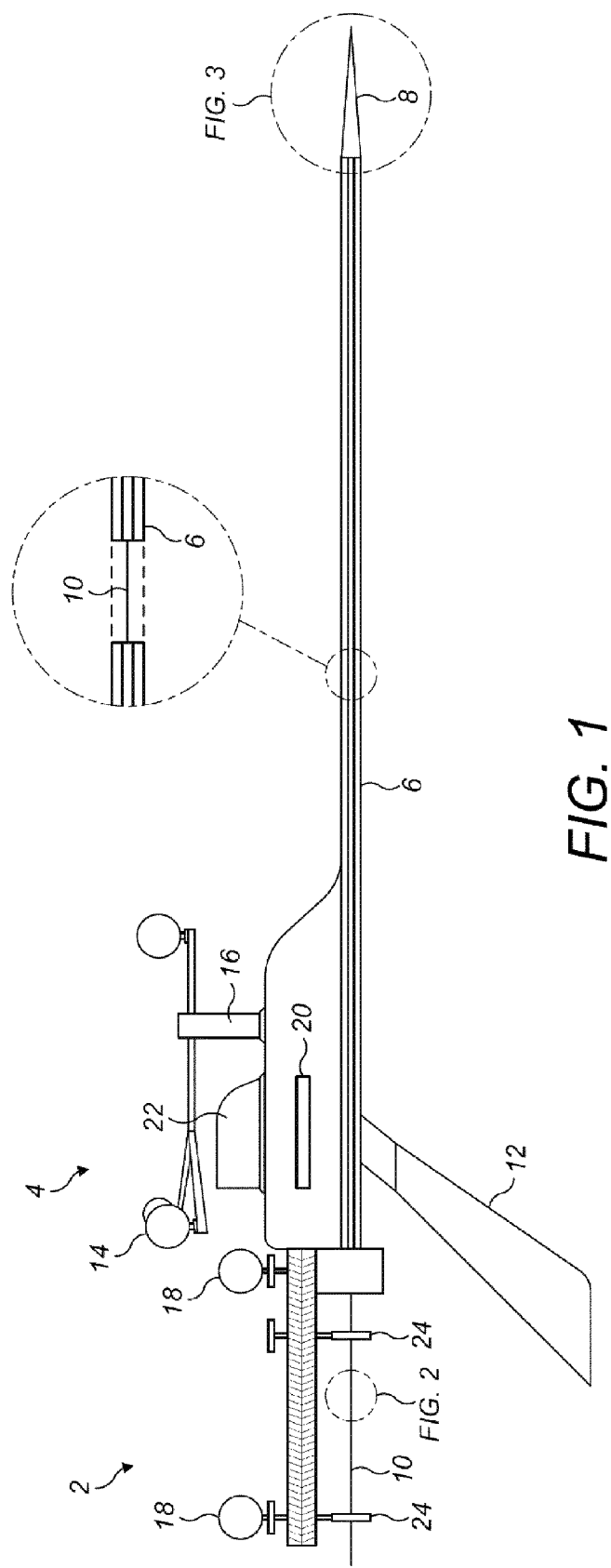
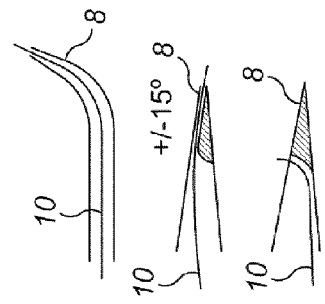
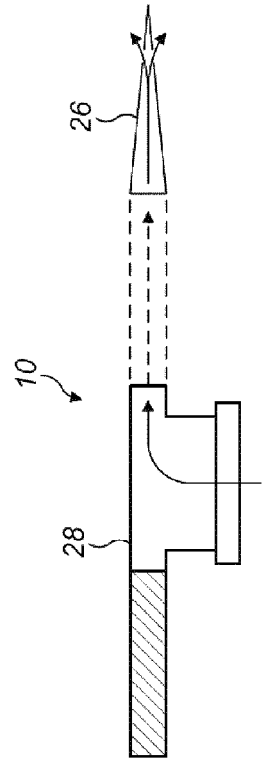

US 9,579,368 B2

TREATMENT OF HEADACHE BY INJECTION OF NEUROINHIBITORY SUBSTANCE TO SPHENOPALATINE GANGLION OR OTIC GANGLION

CROSS-REFERENCE TO RELATED APPLICATIONS

The present application is a U.S. National Phase filing of International Application No. PCT/EP2013/068515, filed on Sep. 6, 2013, designating the United States of America and claiming priority to British Patent Application No. 1215950.5 filed Sep. 6, 2012 and British Patent Application No. 1215949.7 filed Sep. 6, 2012. The present application claims priority to and the benefit of all the above-identified applications, which are all incorporated by reference herein in their entireties.

Aspects of the disclosure relate to a method for prevention or treatment of headache in a patient which involves the injection of a neuroinhibitory substance such as botulinium toxin (often sold under the trade name Botox which is botulinium toxin A) in close proximity to the sphenopalatine ganglion (SPG) or otic ganglion (OG). In particular, the some aspects of the disclosure relate to the injection of the neuroinhibitory substance infrazygomatically or transnasally to allow the neuroinhibitory substance to be delivered in close proximity to the SPG or OG without risk of damaging other critical nearby structures such as the brain and eyes. These administration routes also allow access to the SPG without passing through a large bone.

BACKGROUND

Migraine is a primary headache that may be characterized as a unilateral headache associated with symptoms like nausea, photophobia and phonophobia. More than 50% of migraine sufferers also have cranial autonomic symptoms such as lacrimation, conjunctival injection, nasal congestion and rhinorrhoea.

A possible mechanism for a migraine attack is parasympathetic activation with nitrogen oxide (NO) as transmitter induce dilatation of cranial blood vessels, plasma protein extravasation and release of inflammatory substances. The catalysing enzyme for NO NOS (NO synthases) has been located in perivascular nerve fibres on cerebral arteries and traced back to the sphenopalatine ganglion (SPG) and otic ganglion (OG), as described by Olesen J. in "The role of nitric oxide (NO) in migraine, tension-type headache and cluster headache", Pharmacology and Therapeutics, 2008; 120; 157-171.

Blocking of the SPG by application of lidocaine has shown to be effective in randomised, controlled studies of acute treatment of migraine (see Maizels M, Scott B, Cohen W and Chen W, "Intranasal lidocaine for treatment of migraine: a randomized, double-blind, controlled trial" JAMA, 1996; 276(4):319-21 and Maizels M and Geiger A M, "Intranasal lidocaine for migraine: a randomized trial and open-label follow-up", Headache, 1999; 39(8):543-51). Blocking via botulinum toxin (Botox) is also described in the prior art, for example in U.S. Pat. No. 7,981,433.

The trigeminal autonomic cephalalgias (TACs) are a group of primary headache disorders characterized by unilateral head pain that occurs in association with ipsilateral cranial autonomic features such as lacrimation, conjuctival injection and nasal symptoms. The TACs include hemicrania continua, paroxysmal hemicrania, short lasting unilateral neuralgiform headache with conjunctival injection and tearing/cranial autonomic features (SUNCT/SUNA) and cluster headache.

Cluster headache is a severe unilateral headache associated with ipsilateral autonomic symptoms and characterised by a circannual and circadian periodicity (see Goadsby P J, Cittadini E, Burns B and Cohen A, "Trigeminal autonomic cephalalgias: diagnostic and therapeutic developments" Curr Opin Neurol, 2008; 21:323-330). Approximately 90% suffer from the episodic form and 10% from the chronic form. Based on functional neuroimaging central to the pathophysiology of the disease may be an abnormality in hypothalamic function that facilitate a cascade of metabolic and other biochemical events triggering an attack (see Cohen A S and Goadsby P J, "Functional neuroimaging of primary headache disorders" Expert Rev Neurother, 2006; 6(8):1159-1171). This sets off a positive feedback system involving the trigeminovascular system as the afferent limb and the parasympathetic outflow from the superior salivatory nucleus via the facial nerve through the SPG and OG as the efferent limb (see Goadsby P J, "Pathophysiology of cluster headache: a trigeminal autonomic cephalgia" Lancet Neurol. 2002; 1:251-57). Thus, vasodilatation of the pain-producing large cranial vessels and dura mater starts a reflex activation of parasympathetic vasodilator efferents which activate the trigeminal endings further to produce the excruciating pain and the parasympathetic symptoms (lacrimation and nasal congestionsecretion) seen in cluster headaches. In addition, the carotid swelling leads to a neuropraxic lesion of the sympathetic plexus surrounding the artery, resulting in a partial ipsilateral Horner's syndrome (ptose, miosis and conjunctival injection).

Current strategies for surgical treatment of these headaches include neurodestructive procedures targeting the trigeminal system (afferent limb) and the SPG (efferent limb), and neurostimulating procedures targeting the great occipital nerve and grey matter of hypothalamus (deep brain stimulation, DBS). Thus, cranial autonomic ganglia, and especially SPG and OG, are thought to have a role in the development of primary headaches and treatments have been established targeting the SPG.

Primary headaches may be hard to treat and the need for preventive treatments is enormous. Apart from CGRP antagonism, inhibition of the NO pathway may be considered the best documented and most promising target for treatment of primary headache (as described by Olesen J. in the reference above).

The trigeminal nerve is involved in all types of headache, including secondary headaches, i.e. headaches caused by other pathologies.

Sinonasal polyposis is a chronic hyperplastic disease of the nasal mucosa and the paranasal sinuses. There is a well established association between polyposis and rhinitis. The causes underlying the association could be due to chronic inflammation most likely induced by unstable autonomous nerve control of nasal vasomotor activity. This may precede the occurrence of nasal polyps. Vasomotor rhinitis seems to be related to an imbalance in the cranial autonomic system between parasympathetic and sympathetic activity. Therapies include vidianectomi and other forms of autonomic denervation which blocks parasympathetic activity through the SPG. Vidianectomi and other forms of autonomic denervation have also been an option for treating allergic rhinitis and new modified surgical techniques yield optimistic results.

Blocking the parasympathetic activity passing through the SPG by vidian neurectomy has shown to be effective in allergic rhinitis (see Wan-Fu S U, Shao-Cheng Liu, Feng-Shiang Chiu and Chia-Hsuan Lee. Antegrade transsphenoidal vidian neurectomy: Short-term surgical outcome analysis. Am J Rhinol Allergy 2011; 25:e217-e220), vasomotor rhinitis and rhinosinusitis with polyposis (see Cassano M. Mariano G. Russo L. Cassano P. Sphenopalatine artery ligation with nerve resection in patients with vasomotor rhinitis and polyposis: a prospective, randomized, double-blind investigation. Acta Oto-Laryngologica 2012; 132(5): 525-32).

Almost all patients who undergo parotidectomy will to some extent develop Frey syndrome (auriculotemporal syndrome or gustatory sweating) after surgery, because of aberrant regeneration of cut parasympathetic fibers between otic ganglion and subcutaneous vessels. Frey syndrome may also occur after extirpation of the submandibular gland, mandibular condylar fracture, and obstetric trauma caused by forceps. Nontraumatic causes are sympathectomy, autonomic neuropathy in diabetes mellitus, herpes zoster infection, and metabolic diseases. Frey syndrome may cause considerable social embarrassment and social incapacity due to profuse flushing and sweating when eating. Blocking the parasympathetic activity through the OG may constitute an effective treatment for these patients.

The cranial autonomic ganglia, and especially the SPG and the OG, are hence interesting targets for treating such entities, but they are not easily reached for interventions such as infiltration with pharmacological substances.

There are four paired cranial parasympathetic ganglia: sphenopalatine (pterygopalatine) ganglion (SPG), otic ganglion (OG), ciliary ganglion, and submandibular ganglion.

The SPG is pyramid shaped with a mean diameter of 3.5 mm. It is suspended from the maxillary nerve by the sphenopalatine nerves. Preganglionic parasympathetic fibres form the nervus intermedius of the facial nerve synapse with postganglionic fibres innervating the lacrimal gland, mucosa of the sinonasal cavity and cerebral blood vessels. Postganglionic sympathetic fibres from the superior cervical ganglion pass through the ganglion as well as sensory nerves from the maxillary nerve that innervates the palate and the epipharynx. The SPG can be identified using MRI.

The SPG is situated in the sphenopalatine (pterygopalatine) fossa (SF) and has the shape of a funnel flattened in the coronal plane. It is wider superiorly and then narrows down inferiorly with the apex pointing downwards into the greater palatine canal. The SF has the following boundaries; superiorly with the infraorbital fissure, laterally with the pterygomaxillary fissure, medially with the palatine bone, posteriorly with the pterygoid plates, anteriorly with the posterior wall of the maxillary sinus and inferiorly with the palatine canal. Additionally, it communicates with the nasal cavity through the sphenopalatine foramen and the middle cranial fossa through the vidian canal and foramen rotundum. It can be divided in three compartments, an anterior compartment containing mainly blood vessels, a middle compartment containing mainly adipose tissue, and a posterior compartment containing mainly neural structures.

The maxillary artery enters the SF through the pterygomaxillary fissure and branches into the sphenopalatine artery, descending palatine artery, infraorbital artery, alveolar arteries and the artery of the pterygoid canal. The SF is often devoid of endoscopic identifiable veins. Blood vessels of the SF are tightly packed as they loop the anterior compartment and therefore a lateromedial intervention is more likely to cause a bleeding than an anteroposterior approach.

The average distance from the SPG to the vidian canal is 2.7 mm, to the infraorbital fissure 20.3 mm and to foramen rotundum 4.7 mm. It is normally located in the same vertical and horizontal plane as the vidian canal and posteriorly for the sphenopalatine foramen. The sphenopalatine foramen is vertically orientated located in the superomedial corner of SF with a diameter of 5-6 mm and typically located below the posterior end of the line of attachment of the middle turbinate and crista ethmoidalis, but this may vary. The average distance from the piriform aperture is 48 mm with an angle of elevation from the nasal floor is 22 degrees.

Such information of the distances from SPG to landmarks identifiable on CT may be used to mark the SPG for image-guided interventions when MRI is contraindicated or not available.

OG is an oval structure measuring approximately 4 mm×3 mm×1.5 mm. It is composed of parasympathetic fibre arising in the inferior salivatory nucleus in the medulla, sympathetic fibres form the superior cervical sympathetic ganglion, and motor fibres from the mandibular branch of the trigeminal nerve. The OG supplies secretory and sensory fibres to the parotid gland and parasympathetic fibre to cerebral blood vessels. It is situated just posterior of the lateral pterygoid plate below the foramen ovale in the infratemporal fossa and adjacent to the middle meningeal artery, mandibular nerve and buccal nerve.

The inventors have realised that for a minimally invasive interventions in the SF there are three surgical approaches, each with its advantages and disadvantages; a lateral approach through the pterygomaxillary fissure, a medial transnasal approach through the sphenopalatine foramen and a transoral approach through the greater palatine canal. All approaches give relatively easy access to SF for someone skilled to the art, but the present inventors have realised that there are pivotal differences if a high-precision intervention in the close proximity of the SPG is needed. For example, the SF is filled with fat through which substances such as botulinium toxin diffuse slowly. You cannot therefore inject botulinium toxin into the SF in the hope that it might eventually diffuse to the SPG. The present inventors have realised that you need to inject the botulinium toxin in close proximity to the SPG and therefore you need to know where the SPG is. The SPG can be located with MRI and targeted using image guided surgery (IGS).

IGS was developed to improve accuracy and precision. Such technology is used to assist in orientation by displaying the position of a pointer or surgical instrument on a medical image. Armless systems may be based on light, sound waves or magnetic fields. With the use of a computer platform, a tracking system and a body marker, a pointer or other instrument can be calibrated so that the navigation system will display the tip of the instrument correctly. The instruments are calibrated in advance by the manufacturer or the surgeon may use a universal instrument integration system to calibrate basically any instrument. This system is based on a set of universal clamps attached to the instrument. There are several limitations to this solution. Firstly, attaching the clamps can be challenging and they can easily move, hence giving a wrong impression of the actual localization of the instrument on the medical image. Secondly, semi-rigid instruments are not suitable for calibration because they can bend after calibration, such as e.g. a thin needle or a long forceps.

The present inventors have realised that for a high-precision intervention near to the SPG an infrazygomatic approach is preferred. Moreover, this can be carried out under local anaesthesia. Using the infrazygomatic approach there is a straight line through soft tissue from the skin to the SF, SPG, orbita and the sphenopalatine foramen. The distance from the skin to the SF or SPG is approximately 6-9 cm making it next to impossible to achieve a high precision infiltration without the use of IGS.

The inventors have been able to localize the SPG on MRI and are therefore able to determine the exact location of SPG in any patient. 3D reconstruction of fusioned MRI and CT images is the ideal method for predicting the best approach in every case. This work has made it clear that the suprazygomatic approach has great limitations.

In the suprazygomatic approach, which is described in U.S. Pat. No. 7,981,433, for example, the sphenoid bone will normally obstruct access to SF and always block access to the SPG, making it quite safe, but not applicable for high-precision interventions. Due to the low diffusion rate of botulinum toxin and the fact that the SF mainly contains adipose tissue, a hydrophilic substance injected using these techniques will rarely reach its target.

The inventors have also realised that the medial transnasal approach offers an alternative solution although it is difficult to perform under local anaesthesia due to the sensible posterior region of the nasal cavity, and the use of general anaesthesia makes it much less desirable. Due to the complex sinonasal anatomy the medial transnasal approach is normally performed by a rhinologist. For someone skilled in the art however, this approach is the most accurate, mainly due to the low distance between the puncture site and the SPG. Normally such an approach is done by advancing the needle through the sphenopalatine foramen, risking damage to the sphenopalatine arteryarteries. The palatine bone, which constitute the anterior border of the sphenopalatine foramen, is quite thin, and a suitable needle can quite easily be advanced through the bone, avoiding possible damage to the sphenopalatine artery.

The transoral approach can be done with local anaesthesia. However, due to the direction of the palatine canal towards the very anterior part of the SF, high-precision interventions targeting the SPG are not feasible with this approach.

Intervention targeting OG can be done via a lateral approach as described in interventions targeting the trigeminal ganglion through the oval foramen, or lateral approaches with the same injection sites as described above, i.e. infrazygomatic or suprazygomatic. It is also possible to apply a transnasal medial image-guided approach through the ostium and the posterior wall of the maxillary sinus and advancing adjacent to the lateral pterygoid plate. With this transnasal medial approach one can avoid important nerves and blood vessels and was performed without complications or side effects.

The cranial parasympathetic ganglia including the SPG and OG are surrounded by critical neural structures and organs like e.g. brain and eyes. Drug impact of these structures can cause serious complications and should be avoided. In addition, some medications diffuse slowly and they must be injected with millimetre accuracy to reach their target. As a result, accuracy is important in various situations:

1) When using a drug or implant that only works exactly where it is injected/situated 2) Use of a diffusible drug that must be injected at a safe distance from sensitive structures (e.g. brain or eye)

3) When using a drug or implant that can cause serious complications if it is injected accidentally in the wrong place.

4) For injection into an area where the needle can damage other nearby structures.

All four factors are important when it comes to injections of botulinum toxins or similar neurotoxins to the SPG or OG, and some or all of the factors also apply to other medications that one can envisage using in blocking of cranial parasympathetic ganglia.

As noted above, prior art such as U.S. Pat. No. 7,981,433 discloses administration (topical and by injections) of neurotoxins (e.g. Botox) to parasympathetic (including SPG), trigeminal and occipital nerves in the treatment of headaches amongst other things.

U.S. Pat. No. 7,981,433 describes an injection technique, specifically a lateral approach, which is a conventional suprazygomatic approach. This approach makes it impossible to accurately deposit substances, since the sphenoid bone will normally obstruct access to the sphenopalatine fossa and always to SPG, making it quite safe, but not applicable for high-precision interventions. Due to the low diffusion rate of botulinum toxin and that the SF mainly contains adipose tissue, a hydrophilic substance will rarely reach its target. There is no consideration in U.S. Pat. No. 7,981,433 of the techniques required to reach other parasympathetic ganglia (most importantly OG).

Thus, there is a significant unmet need for a safe, high-precision system for targeting of cranial parasympathetic ganglia in the human or animal body with pharmaceuticals.

SUMMARY

Viewed from a first aspect, certain embodiments provide a method for treating or preventing headache in a patient such as a human in need thereof comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from another aspect, certain embodiments provide a neuroinhibitory substance for use in a method for treating or preventing headache comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from another aspect, certain embodiments provide a neuroinhibitory substance for use in treating or preventing headache wherein said treatment or prevention comprises injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from another aspect, certain embodiments provide a neuroinhibitory substance for use in the manufacture of a medicament for treating or preventing headache said use comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from another aspect, certain embodiments provide botulinium toxin for use in a method for treating or preventing headache comprising injecting botulinium toxin in close proximity to the sphenopalatine ganglion or otic ganglion wherein an injection device comprising said botulinium toxin is brought into close proximity to the sphenopalatine ganglion or otic ganglion by inserting said injection device into the patient transnasally or infrazygomatically and the botulinium toxin injected in close proximity to the SPG or OG.

Viewed from another aspect, certain embodiments provide a method for treating or preventing rhinitis, rhinosinusitis, Frey syndrome or hypersecretion of tears in a patient such as a human in need thereof comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

Viewed from another aspect, certain embodiments provide a neuroinhibitory substance, such as botulinium toxin, for use in a method for treating or preventing rhinitis, rhinosinusitis, Frey syndrome or hypersecretion of tears comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and the neuroinhibitory substance injected in close proximity to the SPG or OG.

DETAILED DESCRIPTION

Aspects of this disclosure relate to the injection of neuroinhibitory substances such as botulinium toxin in close proximity to the SPG or OG. Note that the injection device should not penetrate the SPG or OG. The injection is achieved in order to treat or prevent headache and may be achieved without damage to surrounding critical structures within the head. A neuroinhibitor is defined as any substance that affects transmission in a neural structure, resulting in any change of transmission, that may decrease or increase the neural activity. The neuroinhibitory substance is preferably a neurotoxin.

By delivery of the active substance in close proximity to the sphenopalatine ganglion or otic ganglion means that the botulinium toxin or other neuroinhibitory substance in question is delivered so close to the SPG or OG that it causes the desired technical effect, e.g. the prevention or treatment of headache etc. Ideally therefore the neuroinhibitory substance is injected to within 5 mm of the SPG or OG, preferably within 4 mm, such as within 3 mm, especially within 2 mm. Ideally injection of the active ingredient takes place 2 mm or less form the target SPG or OG. This can be measured using the device and associated computer technology which is described in detail below.

In order to ensure that injection takes place in close proximity to the SPG or OG it is possible to use surgical navigation equipment (or image guided surgery procedures) to aid the operator in positioning the needle.

Thus, viewed from another aspect, certain embodiments provide a neuroinhibitory substance for use in a method for treating or preventing headache comprising injecting a neuroinhibitory substance such as botulinium toxin in close proximity to the sphenopalatine ganglion or otic ganglion wherein an injection device comprising said neuroinhibitory substance is brought into close proximity to the sphenopalatine ganglion or otic ganglion by inserting said injection device into the patient transnasally or infrazygomatically and surgically navigating said device into close proximity to the sphenopalatine ganglion or otic ganglion and injecting the neuroinhibitory substance in close proximity to the SPG or OG.

The injection of the neuroinhibitor must occur infrazygomatic or transnasally in order to ensure that a safe, close injection of the neuroinhibitor is achieved. The terms infrazygomatic or transnasally are terms of this art.

The term infrazygomatic therefore requires that the injection takes place inferior to the zygomatic arch on either side of the mandibula, typically anterior or through the mandibular notch. FIGS. 10a and b show the location of the SPG in the head. The device is shown approaching the SPG infrazygomatically. FIGS. 12a and b show the infrazygomatic approach to the OG with straight line application.

The term transnasally defines an injection route which involves advancing the needle through the nasal cavity. Targeting the SPG this route will further violate the lateroposterior boundary of the nasal cavity, constituting the medial boundary of the SF. FIG. 11 shows the transnasal approach with angled needle. The needle passes through the nasal cavity and therefore only penetrates the mucosa at the shown point.

Targeting the OG involves advancing through the maxillary ostium and the maxillary sinus, violating the back wall of the maxillary sinus, advancing on the lateral aspect of the lateral pterygoid plate. The OG is located in the infratemporal fossa, the SPG in the sphenopalatine fossa. FIG. 13 shows a transnasal straight line approach.

It is preferably the case that access to the SPG or OG from the outside of the body is achieved infrazygomatically or transnasally by insertion of the injection device such that the device defines a straight line between SPG or OG (or more specifically the point close to the SPG and OG where active substance release will occur) and the point at which the external skin or mucosa is penetrated. This is illustrated in FIGS. 10, 12 and 13. FIG. 11 shows an alternative preferred approach where the end piece of the device has a curved tip enabling the needle to be directed toward the SPG or OG at an angle from the main axis of the lumen. The device punctures the wall of the nasal cavity at puncture site 50 and the angled tip directs the needle toward the target site.

The infrazygomatic approach therefore allows the injection device to pass through the skin and then soft tissue to the SPG or OG. That can be achieved in a straight line and hence with a straight injection device. That means that the injection can be targeted very accurately in close proximity to the SPG or OG. This method of administration allows application under local anaesthetic.

Where the injection takes place transnasally the route involves passing through the nasal mucosa and the sphenopalatine foramen or the perpendicular plate of the palatine bone to reach the SPG. Injection is not therefore lateral (via the cheek) but preferably involves a straight line from the injection point to the SPG. Transnasal route to reach the OG involves advancing through the maxillary ostium and the maxillary sinus, violating the back wall of the maxillary sinus, advancing on the lateral aspect of the lateral pterygoid plate. This involves a straight line from the injection site to the OG. These methods may require general anaesthesia.

Certain aspects of this disclosure relate to the treatment or prevention of headaches, in particular any kind of primary headache or secondary headache. The treatment or prevention may relate therefore to cluster headaches, migraine, tension-type headache, short lasting unilateral neuralgiform headache with conjunctival injection and tearing /cranial autonomic features (SUNCT/SUNA), hemicrania continua or paroxysmal hemicrania.

Paroxysmal hemicrania is a primary headache disorder involving frequent attacks of unilateral, peri-orbital and temporal pain typically lasting less than 30 minutes. The pain can be associated with conjunctival injection, lacrimation, nasal congestion, rhinorrhea, ptosis and eyelid edema.

SUNCT/SUNA is a primary headache disorder characterized by multiple attacks of unilateral, peri-orbital and temporal pain typically lasting less than 2 minutes. The pain is associated with conjunctival injection, lacrimation, nasal congestion, rhinorrhea, and eyelid edema. This headache may be associated with trigeminal neuralgia.

Hemicrania continua is a primary headache disorder characterized by a strictly unilateral headache responsive to Indomethacin. The pain is associated with conjunctival injection, lacrimation, nasal congestion, rhinorrhea, ptosis, and eyelid edema.

It will be appreciated that the term treatment here refers to reduction in pain experienced by a patient and/or a reduction in the frequency in which headache occurs. The term prevention means preventing headaches occurring, e.g. as frequently as before.

The neuroinhibitory substance is one which is capable of preventing or treating headache when administered in close proximity to the SPG or OG. Suitable inhibitors include Botulinum toxin e.g. type A, Tetanus neurotoxin, (which is produced by *Clostridium tetani*), Staphylococcal alpha-toxin, and acylpolyamine toxins (e.g. AR636 and AG489).

In general the therapeutic modality used to treat and/or prevent headache is a presynaptic neurotoxin. "Presynaptic neurotoxin" as used herein refers to those neurotoxins and their derivatives which are known to produce localized, reversible flaccid paralysis of musculature in mammals which does not result in degeneration of muscle or nervous tissue.

It is preferred however if the inhibitor is botulinum toxin. This is a protein and neurotoxin produced by the bacterium *Clostridium botulinum* and is commercially available. It is preferred if the botulinum toxin is of types A, B, C, D, E, F or G, such as Botulinum toxin type A. Botulinum toxin may for example be administered in the manner and form described in U.S. Pat. No. 7,981,433.

The presynaptic neurotoxins will be preferably administered as a composition in a pharmaceutically suitable carrier. For this purpose, presynaptic neurotoxin compositions will be prepared for administration by combining a toxin of the desired degree of purity with physiologically suitable sterile carriers. In a preferred embodiment, the preparation of such compositions typically involves mixing the presynaptic neurotoxin with buffers, antioxidants such as ascorbic acid, low molecular weight (less than about 10 residues) polypeptides, proteins, amino acids, carbohydrates including glucose or dextrins, chelating agents such as EDTA, glutathione and other stabilizers and excipients.

To facilitate administration, the presynaptic neurotoxins can be formulated in unit dosage form. The presynaptic neurotoxins may be supplied, for example, as a sterile solution in a vial.

In general, the amount of presynaptic neurotoxins used for treatment will be determined by the age, gender, presenting condition and weight of the patient, in consideration of the potency of the presynaptic neurotoxin. The potency of a toxin is expressed as a multiple of the LD50 value for a reference mammal. One "unit" of toxin is the amount of toxin that kills 50% of a group of mammals that were disease-free prior to inoculation with the toxin. For example, one unit of Botulinum toxin is defined as the LD50 upon intraperitoneal injection into female Swiss Webster mice weighing 18-20 grams each. One nanogram of the commercially available Botulinum toxin type A typically contains about 40 mouse units. The potency in humans of the Botulinum toxin type A product currently supplied by Allergan, Inc. as "BOTOX®" is estimated to be about LD50=2,730 units.

Assuming an approximate potency of LD50=2,730 units, the presynaptic neurotoxin can be administered in a dose of up to about 1,000 units; however, dosages of as low as about 2.5 to 5 units will have therapeutic efficacy. Dosages between 2.5 or 5 units and as high as 250 units will be normally used, and in one embodiment, individual dosages will be of about 25 to 75 units. Typically, the presynaptic neurotoxin will be administered as a composition at a dosage that is proportionally equivalent to a range of between 1 cc-5 cc/100 units, which translate to 100 unitscc-20 unitscc. Adjustment of these dosages depending on the greater or lesser potency of the presynaptic neurotoxins and factors identified above should be easily determined by those of ordinary skill in the art.

In one embodiment, the dosage used will be the lowest one which is still therapeutically effective (i.e., the dosage which results in detection by the patient of a reduction in the occurrence and/or magnitude of headache pain experienced by the patient, even though other symptoms associated with the pain, such as the premonitory aura, may persist). The patient's sensitivity to, and tolerance of, the presynaptic neurotoxin can be determined in the initial treatment by administering a low dosage at one site. Additional administrations of the same or different dosages can be provided as needed.

The frequency of the injections needed may be every 3 to 8 months but will be patient dependent.

Certain embodiments rely on the ability to inject the neuroinhibitory substance, especially botulinium toxin directly into the place where it is needed. The injection device which is used is therefore one which can reliably deliver the active substance accurately and ideally relies on device rigidity. Care must be taken when carrying out example methods of the disclosure, as violating the sphenopalatine foramen could result in a complicated posterior epistaxis. Violating the infraorbital fissure could damage intraorbital tissue. Violating the sphenopalatine foramen and injecting botulinum toxin in the nasal cavity may cause aspiration or digestion of this highly toxic compound. Violating the infraorbital fissure and injecting botulinum toxin may cause diplopia. Accuracy is therefore very important.

This can be achieved using the device described in detail below.

Example methods or uses of the disclosure can be carried out using a device for interventions within the body, the device comprising: an end piece for insertion into the body at a distal end thereof, the end piece including a rigid lumen for holding an instrument and guiding the instrument to the distal end of the end piece; and a body section supporting the lumen and being rigidly connected thereto, the body section including a navigation array for guidance of the device using a surgical navigation system and/or including an anchor point for a standard navigation array.

The device hence includes a rigid lumen for guiding an instrument, such as a needle for example, and delivering it to a point within the body, this lumen being provided in combination with the ability to work with a surgical navigation system to enable the device to accurately target of a location in the body, for example the SPG as discussed above. Whilst navigation arrays are available with clamp type connections that purport to join to any instrument these do not provide a reliable rigid connection and hence movement between the navigation array and instrument leads to inaccuracies. Further, even if it were possible to guarantee accuracy then in the absence of the rigid lumen of examples of the disclosure deformation of the instrument could occur, once again leaving to lack of accuracy. As explained above accurate positioning of the instrument is of paramount importance and without the use of a device that is both rigid and navigable maximum accuracy cannot be obtained.

The distal end of the end piece is the end that is located in the body when in use, with a proximal end of the end piece joining to the body section. The distal end of the end piece may comprise a tip for piercing the body. The tip preferably has a tapered profile narrowing toward a point so that it can easily penetrate body tissues and bone, if transition through body tissue and/or bone is necessary for the selected approach to the desired target site. The end piece may comprise a scale or other marking to show the depth of insertion into the body.

The lumen should be rigid enough to permit placement of a tip of the end piece with millimetre accuracy without deformation as the lumen penetrates the intervening body tissues or navigates through an open cavity such as the nasal cavity, and whilst being subject to bending moments that might arise as it is manoeuvred along the selected approach toward the target site, for example the SPG. For injections towards the SPG an end piece for the medial approach would need to be more rigid than for the lateral approach due to the need for penetration of bone and for a longer end piece. In a preferred embodiment the device is intended for targeting the OG or especially the SPG via a lateral approach and the lumen has a rigidity sufficient to limit deflection of the needle as it advances along the lateral approach to a maximum of 3 mm per 10 cm of length of the needle, preferably a maximum of 2 mm per 10 cm and more preferably 1.5 mm per 10 cm.

Suitable end pieces may have an internal diameter in the range 0.7 to 1.8 mm and a wall thickness of at least 0.05 mm, in some embodiments at least 0.1 mm. Typically the end piece will have a tapered outer diameter, getting thinner toward the distal end. The tapering may have any suitable profile, and in preferred embodiments the end piece will have a region of constant outer diameter at the proximal end, with a tapering region at the distal end. Generally the internal diameter will be constant throughout the end piece. With a tapered outer diameter and constant inner diameter the wall thickness at the proximal end will be larger than the minimum wall thickness, which will be at the distal end. The wall thickness at the proximal end may be at least 0.5 mm, in some embodiments at least 0.75 mm. Typical outer diameters at the proximal end may be in the range 2-4 mm, for example around 3 mm.

A preferred material for the end piece, which will provide the required rigidity with the dimensions mentioned above, is beta titanium. Stainless steel is another possible material.

In general the end piece and/or lumen may be made as rigid as the standard for commercially available navigable instruments on the market. The end piece and/or lumen may have a rigidity that is at least 60% of the rigidity of the instrument sold under the name VectorVision™ Pointer, with blunt end, as supplied by Brain LAB AG of Germany, the rigidity being as measured during a deflection test with the lumen/instrument being supported in cantilever fashion and a load being applied at the tip. The rigidity may be equivalent to or greater than that of the VectorVision™ Pointer.

The navigation array may comprise optical markers or electromagnetic location sensors, for example optical reflectors such as reflector balls or electromagnetic coils. Any suitable navigation array system can be used. The navigation array may comprise a plurality of markers located in plane with one another and at known locations relative to the end piece. In one preferred embodiment there are at least three markers, for example there may be four or five markers. The navigation array should be rigidly connected to the body section and hence rigidly connected to the end piece. The end piece may have a known orientation and size relative to the navigation array, or a calibration sequence may be performed to provide appropriate data concerning the orientation and size of the end piece relative to the navigation array. A rigid and integrated connection of the navigation array with the body section is preferred since this provides the least risk of inaccuracy and in advertent misalignment of the navigation system with the end piece. Alternatively, when an anchor point is provided then the anchor point should be arranged for rigid connection of the navigation array to the body section. The anchor point may, for example, be for connection to an array of the type supplied under the trade names SureTrack® Universal tracker from Medtronic and Brainlab Instrument Adapter System from Brainlab.

In preferred embodiments the navigation array is held in a track on the body section that permits slidable movement relative to the body section, and the navigation array is rigidly connected to the instrument. The array is hence rigidly fixed to the instrument, whilst both the array and the instrument can move relative to the end piece and body section of the device. This means that as the instrument is advanced or retracted through the lumen then the navigation array will remain in the same position relative to the instrument. Guidance of the instrument can be simpler with this approach, and advantageously it facilitates use of the device as a dynamic pointer. For example the instrument could be a rod, which can be placed close to a target site in the body using the rigid lumen, and then advanced more closely to the body without the need to further move the main parts of the device. With this feature the device may also have the capability to lock the navigation array in place in the track in order to permit use in an alternate mode with the navigation array being used to monitor movement of the end piece and the location of the instrument being monitored either by additional navigation devices or by a scale on the device.

Preferably the device comprises a proximal piece for holding a proximal end of the instrument. The proximal piece may be positioned at a proximal end of the end piece and may be connected to the end piece either directly or via the body section. The proximal piece may be mounted to the body section at an opposite end of the body section to the end piece. It is preferred for the proximal piece to comprise parts that are moveable relative to the end piece and are for fixed connection to the instrument. Such parts can be used in the manipulation of the instrument as described below.

In a particularly preferred embodiment the proximal piece comprises one or more clamp(s) for attachment of the instrument. A clamp or clamps may advantageously be provided on the proximal piece to fix the instrument in place relative to the end piece and the distal end thereof.

When the device has been inserted into the body to a suitable point with reference to a target site the instrument can be operated by manipulation of the proximal end of the instrument at the proximal piece. For example, the instrument may be extended from the distal end of the end piece to move it closer to the target site. When the instrument is a needle this allows for highly accurate targeted injection without the risk of damaging the target site with the rigid and larger diameter end piece. A scale is preferably provided on the proximal piece in order to show the movement of the instrument, for example how far the instrument has been inserted.

The proximal piece may comprise two clamps for releasable connection to the instrument, with one clamp slidable relative to the scale and hence useable to indicate movement of the instrument. Alternatively, or in addition, the proximal piece may comprise positional markers, e.g. in the case of an optical system, reflectors, for indicating the distance. For example, a positional marker may slide along the proximal piece connected to an associated one of the clamps, which in turn may be for fixed connection to the instrument during use, so that the positional marker moves along with the instrument. In a preferred embodiment the proximal piece includes a handle, such as a ring piece, for enabling the user to push or pull the instrument with the thumb or a finger.

The moveable parts of the proximal piece, which are for connection to the instrument, may advantageously be connected to the navigation array when the navigation array is held in a track on the body section as described above. Thus, the rigid connection of the navigation array to the instrument may be via a coupling between the moving parts of the proximal piece and the navigation array.

The device may include a chin-stopper to prevent the instrument from being advanced too far into the body.

The device is for cranial use, for example for targeting of the SPG. The device may hence include a lumen and endpiece with sufficient rigidity to advance easily along the selected approach, which in preferred embodiments is the lateral approach. For example the rigidity may be sufficient to limit deflection of the needle as it advances along the lateral approach to a maximum of 2 mm per 10 cm or other deflection value as discussed above.

The end piece may have a tip adapted to bend the instrument as it is pushed through the lumen and out of the tip. For example, the tip may be an angled tip and/or the tip may comprise internal contours within the end of the tip to angulate the needle as it exits a hole at the very end of the tip or as it exits a hole in the side of the tip. A tip angled at 45 degrees may be used for a device intended for the medial transnasal approach to the SPG, since this enables the device to direct a needle or other instrument closest to the SPG. It may be preferred to use internal contours since in comparison to an angled tip there is no additional disruption to body tissue as the end piece is inserted into the body.

The device can advantageously be used with any instrument capable of passing through the lumen. In preferred embodiments, where the device is for injection of substances into the body, the end piece is for receiving and guiding a needle. For some embodiments the lumen is designed to receive an 18G needle or smaller, more preferably a 25G needle or smaller. The needle may be included as a part of the claimed device.

A preferred needle is provided with a needle tip having a slightly rounded end. This acts to minimise the risk of damage to the target site. The needle preferably comprises openings on each side of the tip rather than at the tip end. This means that tissue on either side is infiltrated by the injected pharmacological substance, and additionally decreases the risk for injection of a substance directly into the ganglion. The proximal end of the needle, or some intermediate point of the needle, for example at the body section, may be provided with a luer lock device for connection to an appropriate source of the pharmacological substance.

In a preferred embodiment a vessel such as an ampule or syringe is attached to the needle at the body section or at the proximal piece. With the ampule feature the device may be provided with a locking mechanism to lock the proximal piece and/or the instrument in position, for example using a first lever or actuator, and a second mechanism to aspirate and then inject a substance from the ampule, for example using a second lever or actuator, advantageously there may be two levers of different lengths for ease of operation.

In the pre-operative planning a standard IGS planning station (e.g. iPlan by Brainlab) may be used to define the best choice of injection site (where there is a straight line through soft tissue towards the SPG).

Certain preferred embodiments will now be described by way of example only and with reference to the accompanying drawings in which:

FIG. 1 shows an example of an intervention device in side view;

FIG. 2 is a detail view showing features of a needle used with the intervention device of FIG. 1;

FIG. 3 shows arrangements for the tip of the intervention device of FIG. 1;

Figures 10A, 10B:
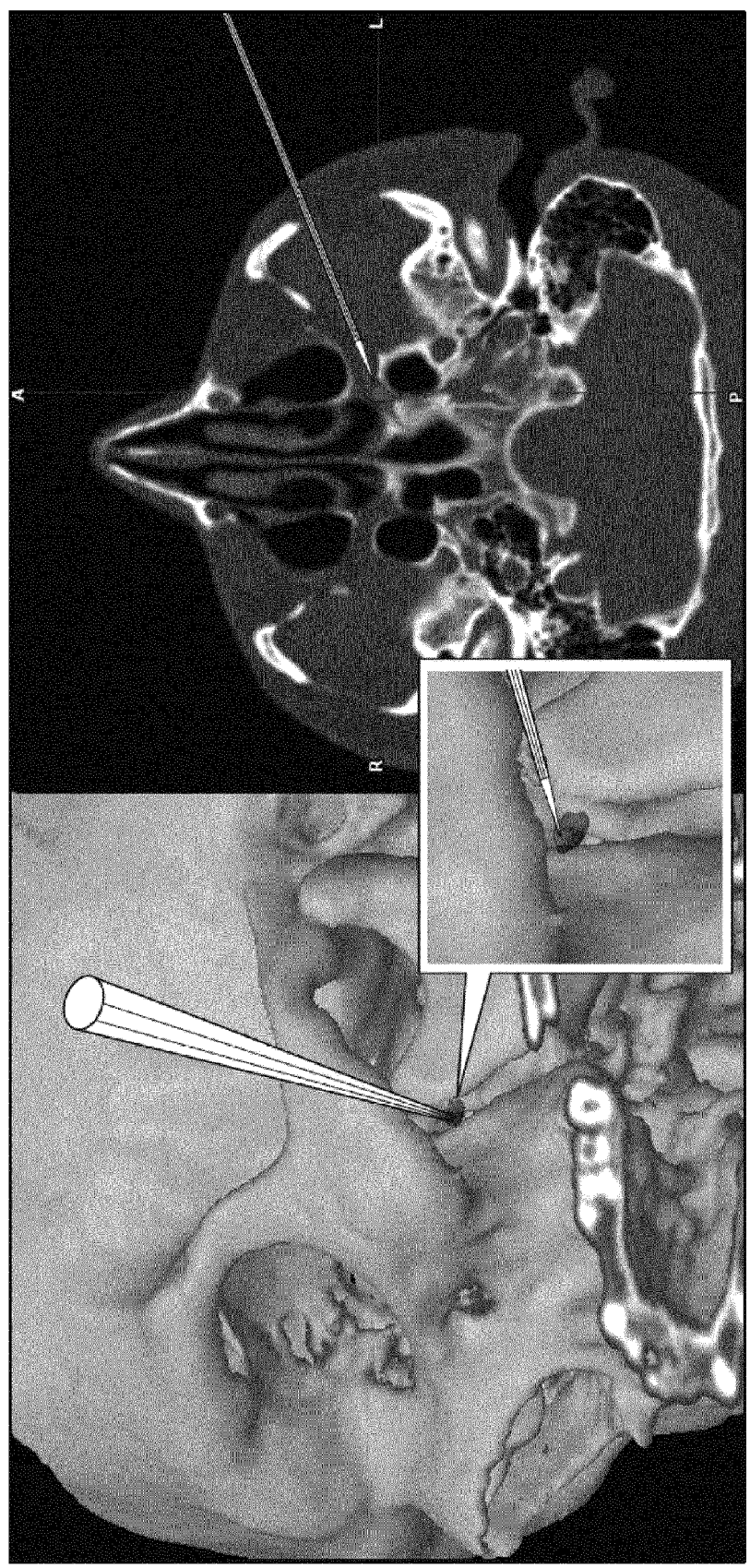
Figure 11:
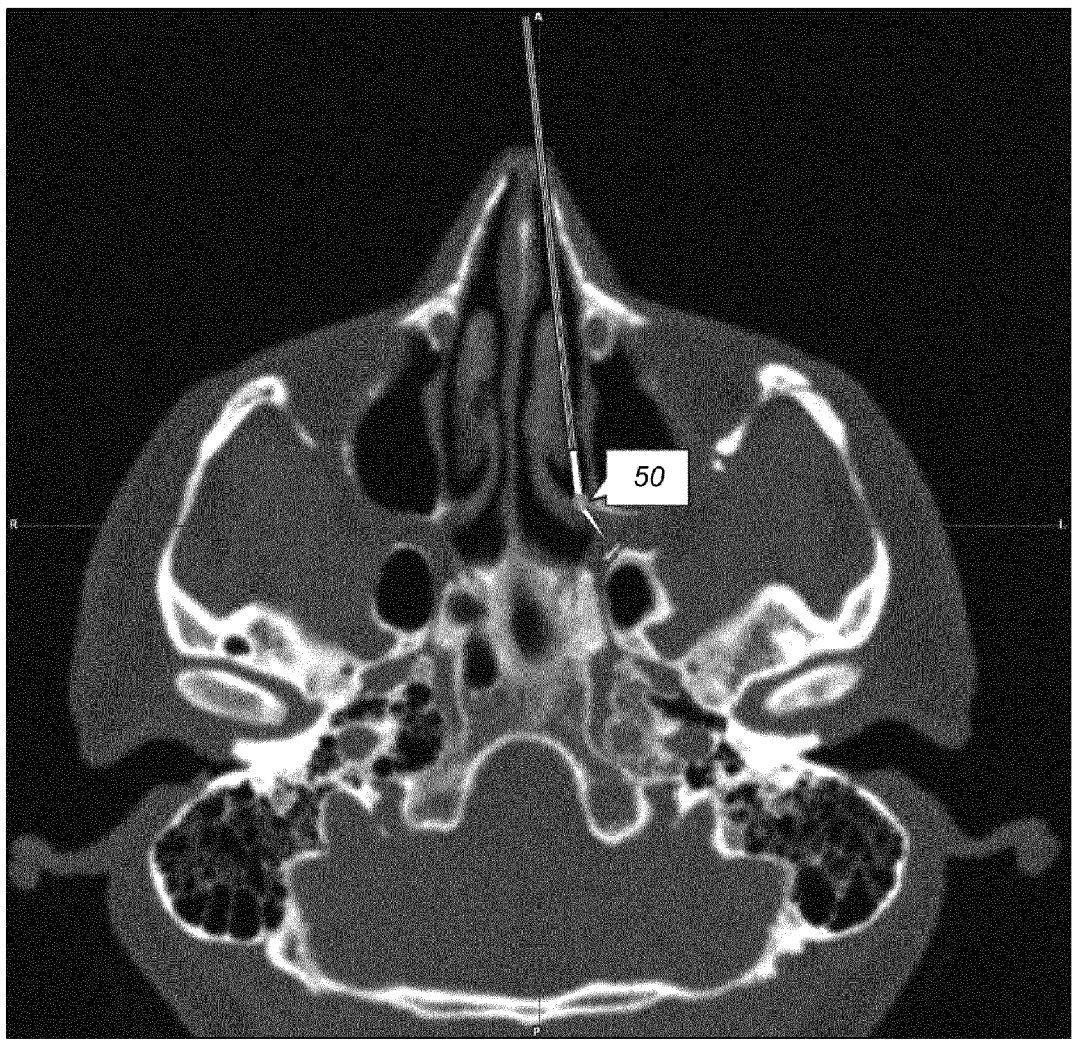
Figures 12A, 12B:
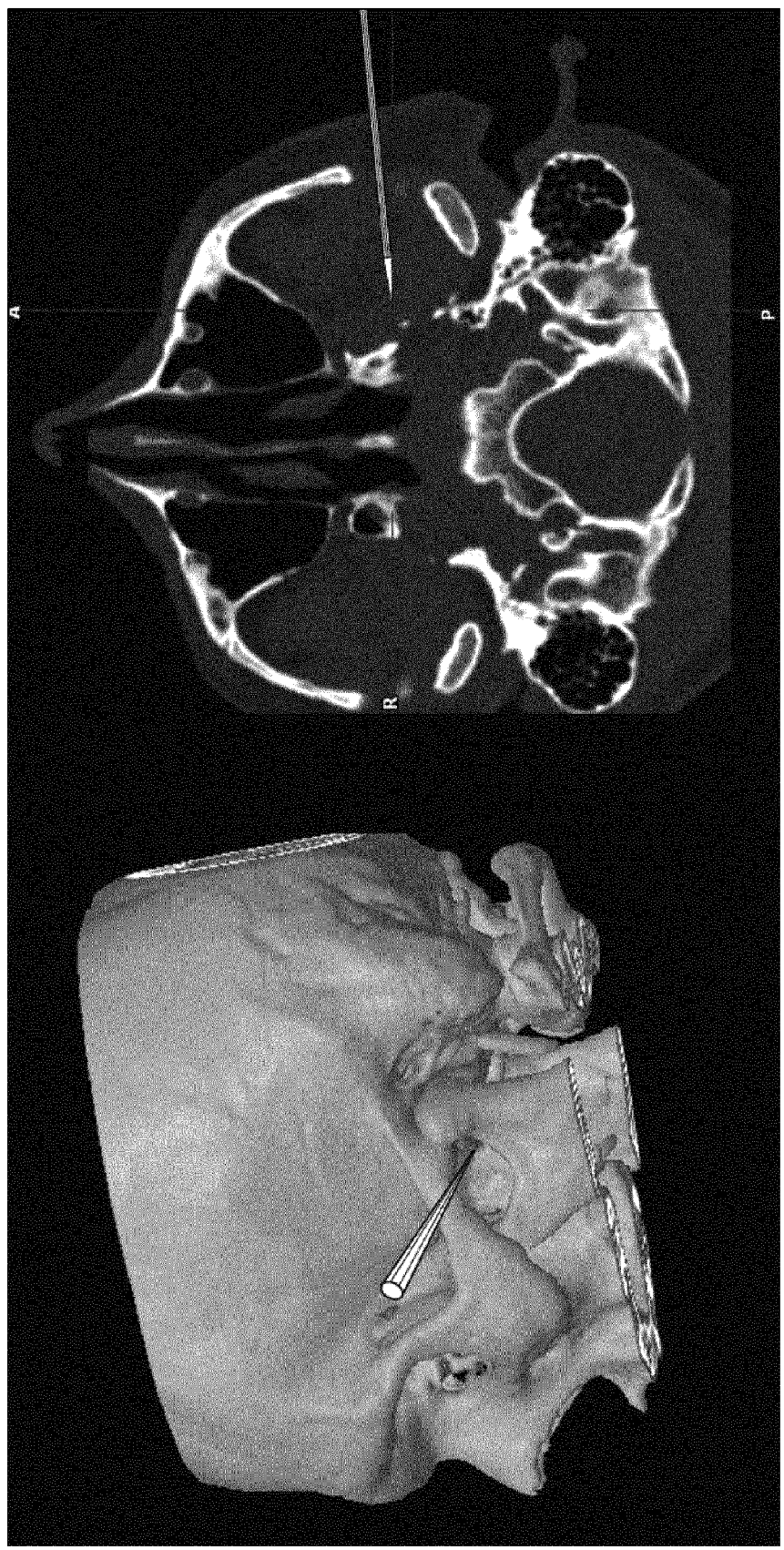
Figure 13:
Figure 14A:
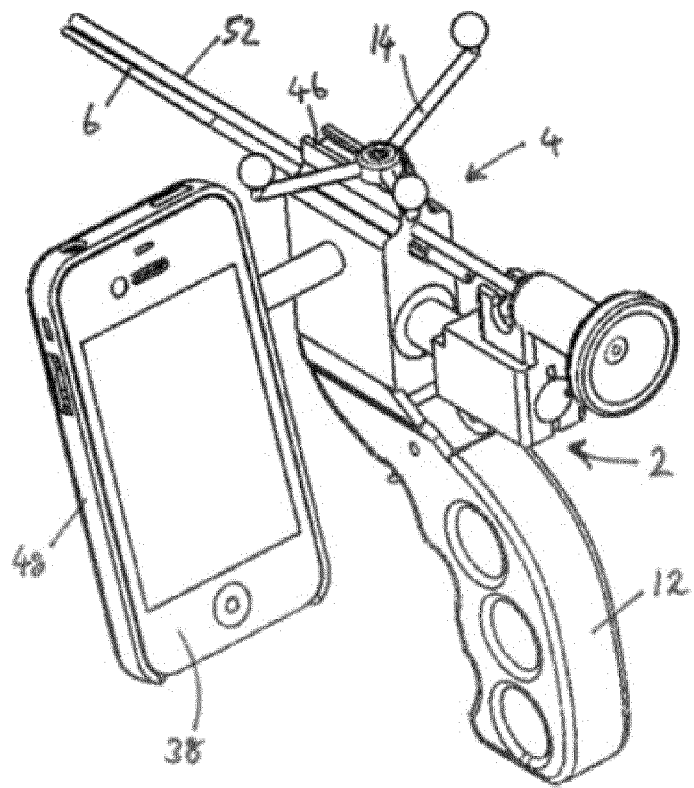
Figure 14B:
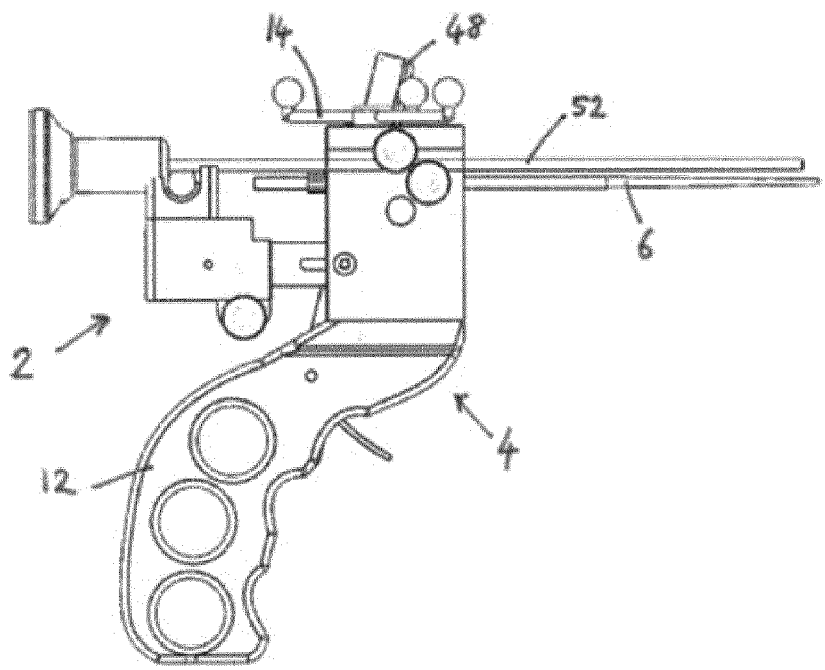

FIGS. 10a and b show the location of the SPG in the head. The device is shown approaching the SPG infrazygomatically;

FIG. 11 shows the transnasal approach with a device having an angled tip, wherein the end piece passes through the nasal cavity and therefore only penetrates the mucosa at the shown point;

FIGS. 12a and b show the infrazygomatic approach to the OG;

FIG. 13 shows the transnasal approach to the OG. The approach is defined by a straight line;

FIGS. 14a and 14b show another example, wherein the intervention device is fitted with an endoscope and smart phone.

FIG. 1 shows an intervention device for high-precision image guided interventions targeting cranial autonomic ganglia. The device can also be used wherever applicable for injections.

The device consists of a proximal piece 2, body 4 and an end piece 6 with a tip 8. It is made of a rigid material to avoid navigation inaccuracy. This is of paramount importance since there is no way for the interventionist to be aware of deformations of an instrument as soon as skin or mucosa is punctured and the instrument is within the body.

The end piece 6 comprises a rigid lumen through which an object such as a needle 10 can pass. The lumen can be of any suitable diameter, length and form, provided that it has sufficient length to penetrate to the injection site. In this example embodiment it is sized for use in a lateral or transnasal medial approach to the SPG and hence the end piece 6 extends away from the body 4 by about 15 cm allowing for sufficient length to penetrate the skin and reach the SPG, which can be perhaps 6 to 9 cm from the skin as noted above. The lumen of the end piece 6 is made of a rigid material to avoid navigation inaccuracy and it should be rigid enough to permit placement of the tip 8 with millimetre accuracy without deformation as the lumen penetrates the intervening body tissues and whilst being subject to bending moments that might arise as it is manoeuvred along the selected approach toward the SPG (which may be transnasal or lateral). The lumen of this example has a diameter just big enough fit a 25G needle with appropriate clearance.

The end piece 6 has centimetre marks to provide an indication of the depth of insertion beneath the skin. The end piece 6 extends through the body 4 and is attached to proximal piece 2 to allow for the needle 10 to extend along the proximal piece as described below. The lumen is open at the proximal end to provide access for the needle 10. The tip 8 can be sharp as shown or rounded to minimize tissue damage. Potential adaptations to the design of the tip 8 are discussed below in relation to FIG. 3. The outer diameter of the end piece 6 may taper off from the proximal end to the distal end of the end piece 6. The very distal end of the end piece may be approximately 20-22G. The inner diameter will typically be just big enough to carry the preferred 25G needle.

The body 4 is connected to and holds the end piece 6 and proximal piece 2. The body 4 includes an ergonomic shaped handle 12 that allows for one-handed use. The body 4 also holds an array 14 with reflector balls for an optical guidance system mounted on a suitable anchor point 16. This optical guidance array 14 can be used in conjunction with further reflector balls 18 mounted on the proximal piece for best accuracy and to permit the navigation system to also monitor the position of the needle 10 within the end piece 6. The body 4 in this example also has a universal clamp anchor point 20, which is formed to fit universal clamps as provided by manufacturers, and also an electromagnetic anchor 22. The various anchor points 16, 20, 22 allow for alternative guidance systems to be used for the needle guide. For electromagnetic navigations system any connection point provided by the manufacturer could be embedded.

The body 4 optionally includes a mounting point (for example, as described below in relation to FIGS. 5 to 7) for a handheld device replacing the traditional computer platform, such as a tablet, smart phone, iPod™ or the like. The display screen of the handheld device can be used during navigation to show the operator what movement of the end piece is required. Such a device can include software that by animation (e.g. three-dimensional) of the medical image with targets and bars, will provide guidance to the operator in relation to the puncture site, alignment of the end piece and distance to the target along with warnings if the device is off track. The software may display a magnified view of a region of interest in the navigation image on the screen of the handheld device. Appropriate software could also be integrated into the software of the computer platform provided by the manufacturers of navigation systems either in addition to software on a handheld device and capable of interacting with the handheld device or as an alternative allowing the use of a separate computer platform without a handheld device. This can make the intervention procedure safer and more precise. Furthermore, it can make the procedure available not only for specialized surgeons but also to surgeons with less experience in this field as well as potentially to other medical professionals such as neurologists and anaesthesiologists. This is of importance since the ease of performing a procedure and hence its availability to patients is as important as the existence of such procedure. The handheld device can communicate with a computer platform through Wi-FI, Bluetooth or the like. The computer platform can be integrated in a tracking rack, making it convenient for storage and transport, and therefore for outpatient use or the like. The device may include a sensor in the body of the device connected to the handheld device that registers movements of the needle and/or of the proximal piece, this is done with or without usage of the possibility of tracking movements by markers on the proximal piece.

The proximal piece 2 is attached to the end piece 6 and the body 4. The proximal piece comprises two clamps 24 for attachment of the needle 10. These clamps 24 are used to fix the needle 10 in place relative to the tip 8. With appropriate guidance from an optical navigation system or similar, the needle guide can be pushed forward using the tip 8 and end piece 6 to penetrate the skin and body tissue. When the tip 8 is at a suitable distance from the target site the distal end of the needle 10 can be extended from the tip 8 by manipulation of the proximal end of the needle 10 at the proximal piece. A scale provided on the proximal piece shows how far the needle has been inserted. In this way the device avoids the risk tissue damage that might otherwise be caused by the larger end piece of the device approaching close to the target site. Extending and then retracting the needle 10 can also be used to avoid backflow of a pharmacological substance as one retracts the device.

Another way to measure the distance that the needle 10 has been moved is the use of positional markers, e.g. in the case of an optical system, reflectors, for calculating the distance. In the embodiment shown one of the reflector balls 18 could slide along the proximal piece 2 connected to an associated clamp 24 and hence provide an indication of the distance that the needle 10 has moved. In such cases, with appropriate software, the position of the needle can be seen on a navigation screen or other computer device.

The device will be made of a rigid material to avoid IGS inaccuracies. Any instrument guided by the device can be semi-rigid, in this case the needle 10, as the device in itself provides the requisite stiffness to ensure that the intervention is accurate.

The needle 10 in this example is a 25G needle that is provided with a specially designed needle tip 26, which is shown in FIG. 2. The tip 26 has a slightly rounded end to minimise the risk of damage to the target site (the SPG in one example) and there are openings on each side of the tip 26 so that tissue on either side is infiltrated by the pharmacological substance. FIG. 2 also shows detail of the proximal end of the needle 10, which is provided with a luer lock device for connection to an appropriate source of the pharmacological substance, for example a syringe.

FIG. 3 shows potential alternative designs for the tip 8 of the lumen, with adaptations to bend the needle 10 as it is pushed out of the tip 8 and to thereby direct it away from the line of the end piece 6. This allows for targeting of injection sites that are not in a location than can be easily accessed in a straight line from an appropriate puncture site. Since the effect of the shaped tip 8 on the final position of the needle 10 as it is extended will be known then the angled path of the needle 10 can be taken into account when the desired path for insertion of the end piece 6 into the body is determined. FIG. 3 shows three possible arrangements, including an angled tip 8, and two systems using internal contours within the tip 8 to angulate the needle 10 either as it exits a hole at the very end of the tip 8 or as it exits a hole in the side of the tip. One advantageous use for an angled tip 8 is shown in FIG. 11, where the SPG is targeted using a transnasal approach.

Figure 4:
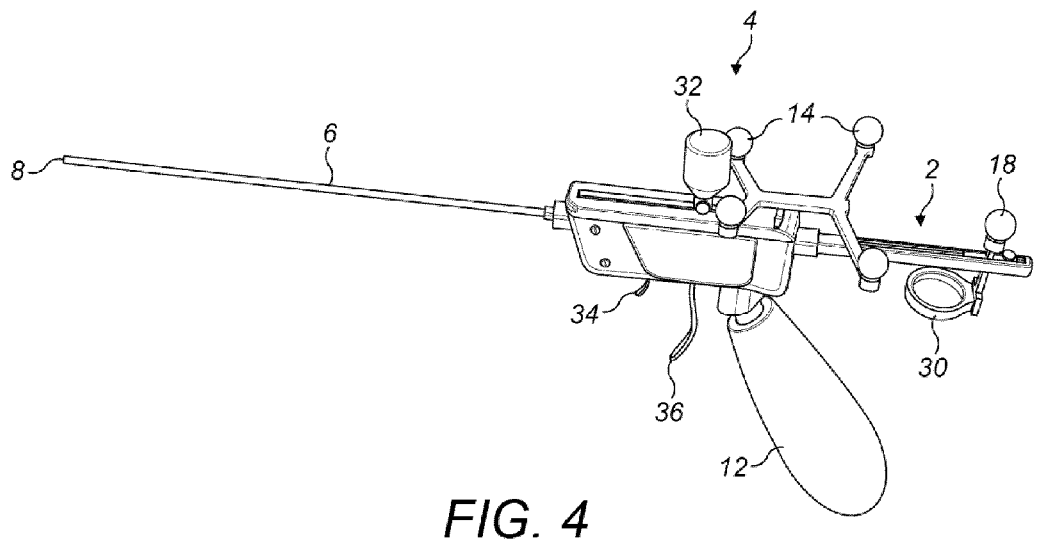
FIG. 4 is a perspective view of another example of an intervention device.
Figure 5:
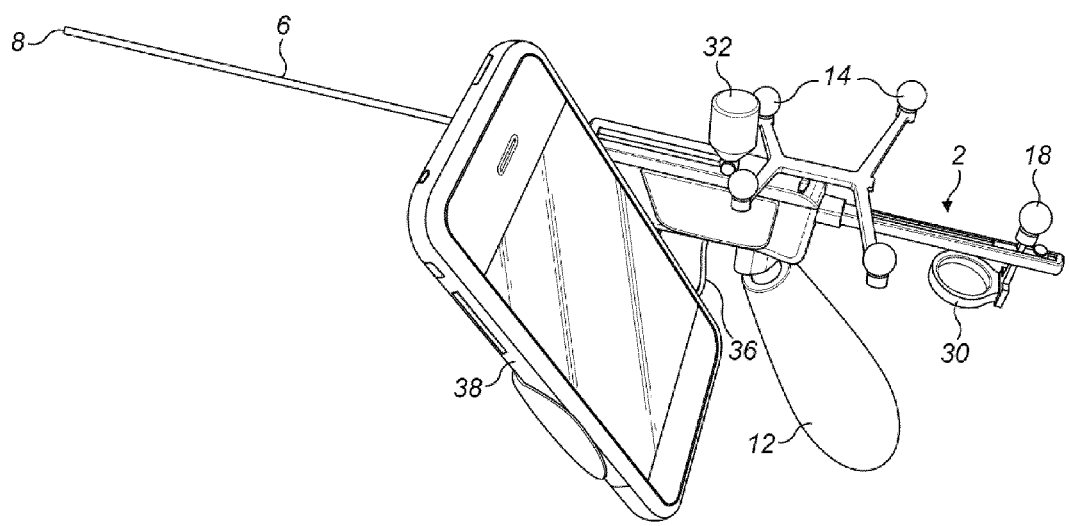
FIG. 5 shows the device of FIG. 4 with the addition of a handheld device mounted to the body of the intervention device.

Another exemplary intervention device is shown in FIGS. 4 and 5. This device has generally similar features to the device described in relation to FIG. 1 and comprises the same main parts, with a proximal piece 2, body section 4 and end piece 6. With the perspective views of FIGS. 4 and 5 the arrangement of the array 14 of reflector balls can be more clearly seen, in particular the spacing of the front and rear pairs of balls 14. This arrangement is also found in the device of FIG. 1.

The example device of FIGS. 4 and 5 includes various additional or alternative features compared to the device of FIG. 1. The differences are in the proximal piece 2 and body section 4, and also in the supply of fluid to the needle. If not described otherwise then the remaining features can be taken to be similar or identical to the features described above for FIG. 1. The proximal piece 2 includes a handle in the form of a ring 30 for enabling the user to push or pull the instrument with the thumb or a finger. In this way the needle can be moved in a one-handed operation whilst the handle 12 of the body section is held by the same hand. A reflector 18 is attached to the ring 30 to permit the navigation system to determine the position of the needle as it moves with movement of the ring 30. To supply fluid to the needle the device of this second example includes an ampule 32 attached to the needle within the body section 4. There are also further features for actuating the device in the form of two trigger levers 34, 36. The body section 4 incorporates a locking mechanism to lock needle in place and prevent further movement of the proximal piece, and this is actuated using a first, shorter, lever 34. A second, longer, lever 36 is provided for actuating a mechanism that aspirates and then injects a substance from the ampule 32.

It will be seen that FIG. 5 includes an additional feature of a handheld device 38, which is not in FIG. 4. The handheld device 38 is mounted to the body section 4 and can operate as discussed above in order to assist the user with navigation.

Figure 6:
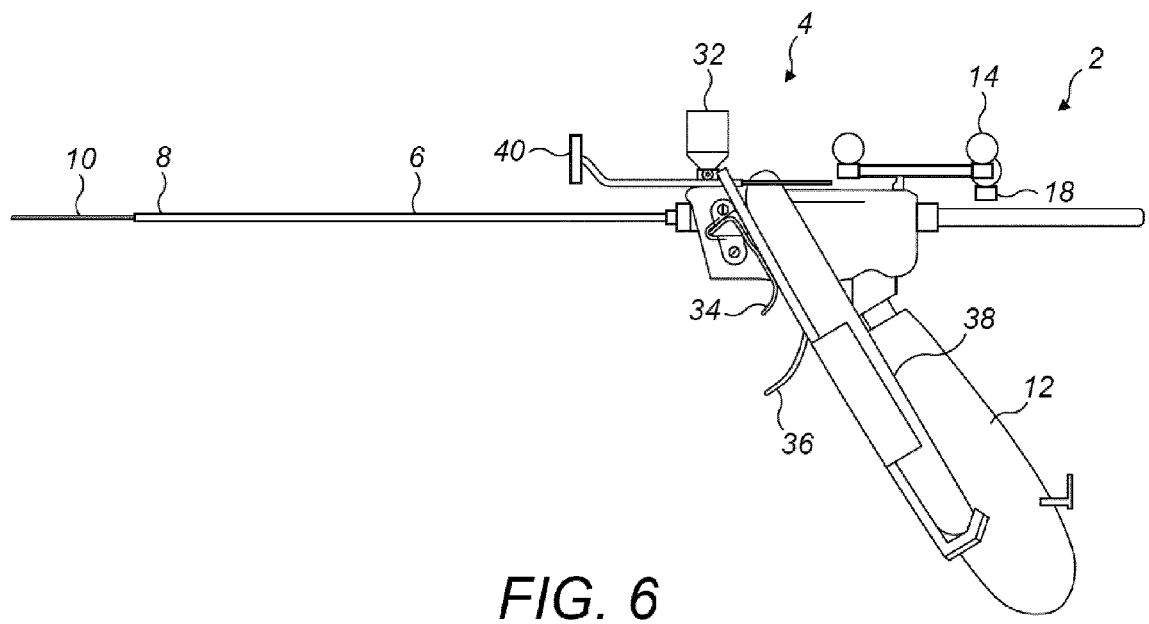
FIGS. 6 and 7 are side and end views of a device similar to the device of FIG. 5.
Figure 7:
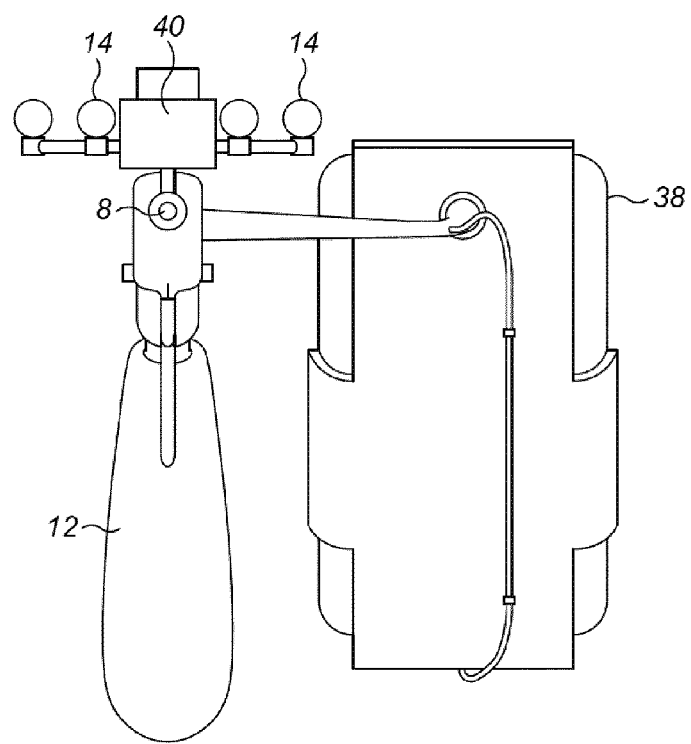

FIGS. 6 and 7 show a similar device to that shown in FIG. 5, but with an additional feature of a chin-stopper 40. The other features are as in FIG. 5, although for this example the ring 30 is omitted. FIG. 6 is a side view and FIG. 7 is an end view looking along the line of the end piece 6 from the tip 8 toward the body section 4. It should also be noted that whilst FIGS. 4 and 5 show the needle 10 in a retracted position, withdrawn within the end piece 6 and hence not visible, FIG. 6 shows the needle 10 extended out of the tip 8 of the end piece 6. The reflector 18 clamped to the needle 10 at the proximal piece 2 is hence moved forward by the same distance that the needle 10 has moved.

Figure 8:
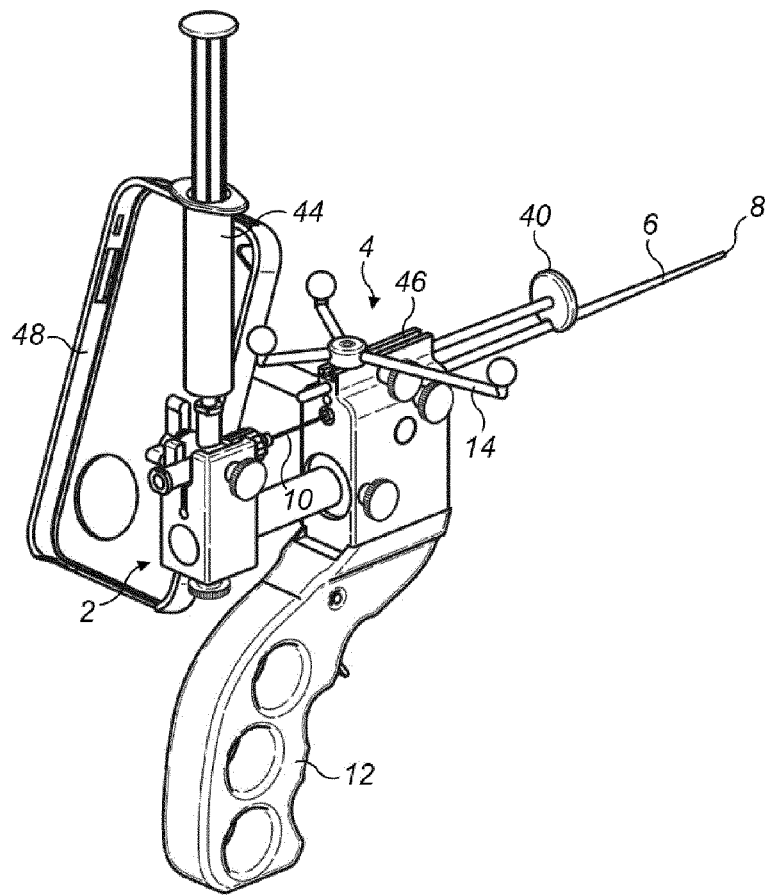
FIGS. 8 and 9 show a further example of an intervention device including an optional cradle for a handheld device and an optional cheek stopper.
Figure 9:
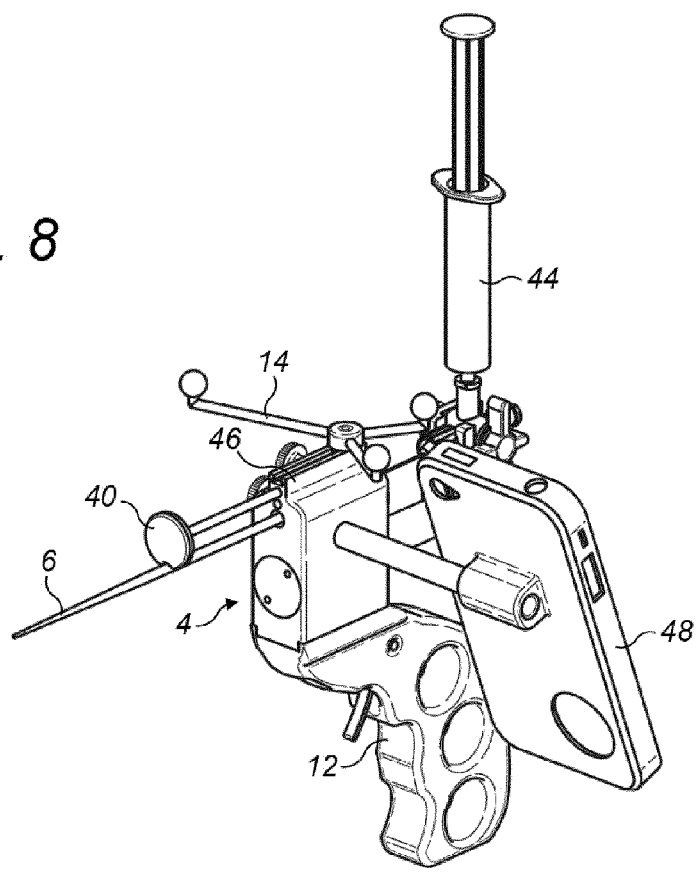

FIGS. 8 and 9 show another example device, which once again is broadly similar to the other examples described herein. In these Figures the reference numbers show similar features to those described above, including the proximal piece 2, body section 4, end piece 6 and tip 8. The navigation array 14 has three reflectors similar to the example of FIGS. 8 and 9. The device of FIGS. 8 and 9 has a syringe 44 connected to the needle 10 via the proximal piece 2. The syringe 44 can be coupled to the needle 10 using any suitable coupling mechanism, for example a three-way stop cock. The device further includes a cradle 48 for a handheld device 38. The handheld device 38 can be used as described above to assist in the intervention procedure. A cheek stopper 40 is also present. It will be appreciated that the device of FIGS. 14*a* and *b* could be used without the cradle 48 and cheek stopper 40, if required.

The device of FIGS. 8 and 9 further includes a track 46 on the body section 4, in which the navigation array 14 is mounted. The track 46 allows the navigation array 14 to slide along the body section, although in the arrangement of the Figures this feature is not in use and the navigation array would instead be fixed in place. When the sliding connection is used the instrument (the needle 10 in this example) would be connected to the navigation array 14 via a coupling between the proximal piece 2 and the array 14. This is to allow the array 14 to be rigidly connected to the instrument and to hence reflect the location of the instrument within the body.

Another example device is shown in FIGS. 14*a* and 14*b*. The main features are similar to the example of FIGS. 8 and 9, but the syringe is not present and instead an endoscope 52 is mounted on the body section 4. Advantageously, the endoscope 52 can be linked to the display of a smart phone 38 mounted in smartphone cradle 48 so that the smart phone 38 shows the endoscope 52 image feed. This allows the view from the endoscope 52 to be easily seen by the user and also to be aligned with the orientation of the device/end piece 6. Fitting the device with an endoscope 52 enables convenient combined use of the endoscope 52 with other instruments, such as a needle 10, without risk of collision of the two instruments.

It should be noted that the features of the needle tip described in relation to FIG. 2 and the various alternative embodiments of the tip 8 of the end piece 6 shown in FIG. 3 can also be utilised in the devices shown in FIGS. 4 to 14. Similarly, the additional features of FIGS. 4 to 14 relating to the handheld device 38/cradle 48, ring 30, ampule 32 and lever system, sliding track 46, syringe 44, endoscope 52 or cheek stopper 40 and so on can also be used with the device of FIG. 1 or as optional features for any of the other devices of FIGS. 2 to 14.

The devices described above makes it safe to use the lateral approach targeting the SPG, significantly lowering the risk of complications such as tissue destruction of adjacent structures by the very instrument at use or adverse events due to misjudged placement of the needle while injecting the pharmacological substance. At the same time the positioning of the injection will be highly accurate, making it feasible to use small volumes with minimal possibilities of diffusion into adjacent structures. Such a precision also ensures optimal delivery of the pharmacological substances and therefore optimal treatment effect.

The end piece 6 can also be adjusted in design by providing it with anchor points for flexible or rigid endoscopes. Use of an endoscope facilitates localisation of the best entry point on the lateral wall of the nasal cavity when using the transnasal route, making the procedure more user friendly and more accessible as the procedure could be performed under local anaesthesia. An endoscope may alternatively be mounted on the body section of the device. In the case of electromagnetic navigation, which can be used as an alternative or in addition to optical navigation, a coil can be embedded in the tip 8 and/or the end piece 6.

Example dimensions for the end piece are set out in the table below. The example end pieces are manufactured of beta titanium and available from Futaku Precision Machinery Industry Company of Kyoto, Japan. Alternative sizes could of course be used, provided that they have sufficient rigidity.

| Straight/ angled tip | Length | | Outer diameter | | Inner diameter (mm) |
|---|---|---|---|---|---|
| | To the angled segment (cm) | Total (cm) | Proximal (mm) | Distal (mm) | |
| Straight | | 14 | 3.048/1.651 | 1.10 | 0.9 |
| 45 degrees | 14 | 16 | 3.048 | 1.270 | 1.1 |
| Straight | | 16 | 3.048 | 1.40 | 1.1 |
| 20 degrees | 14 | 16 | 3.048 | 1.651 | 1.3 |
| 40 degrees | 14 | 16 | 3.048 | 1.70 | 1.6 |
| Straight | | 16 | 3.048 | 1.270 | 0.9 |
| 20 degrees | 14 | 16 | 3.048 | 1.270 | 1.1 |
| 40 degrees | 14 | 16 | 3.048 | 1.45 | 1.3 |
| Straight | | 18 | 3.048 | 2.10 | 1.6 |

Whilst the disclosure has been described in relation to headache, it is also believed that rhinitis, rhinosinusitis, Frey syndrome or hypersecretion of tears/lacrimation can be treated or prevented using the same active agent and mode of administration.

In particular therefore, viewed from another aspect, examples of the disclosure provide botulinium toxin for use in a method for treating or preventing rhinitis, rhinosinusitis, Frey syndrome or hypersecretion of tears comprising injecting botulinium toxin in close proximity to the sphenopalatine ganglion or otic ganglion wherein an injection device comprising said botulinium toxin is brought into close proximity to the sphenopalatine ganglion or otic ganglion by inserting said injection device into the patient transnasally or infrazygomatically and the botulinium toxin injected in close proximity to the SPG or OG.

The rhinitis in question might therefore be
Allergic rhinitis
Vasomotor rhinitis
Rhinitis medicamentosa
Polypous rhinitis
Any kind of non-structural rhinitis
Rhinosinusitis
  Without polyps
  With polyps
  Any kind of rhinosinusitis It is particularly preferred if the SPG is targeted as a therapy for rhinitis, rhinosinusitis and hypersecretion of tears. Targeting of the OG is preferred for the treatment of Frey syndrome.

Whilst examples of the disclosure have been described in relation to the administration of neuroinhibitory substances such as botulinium toxin, the method of injection discussed here can be used for the injection of other active substances such as local anaesthetics (e.g. lidocaine or marcain) and corticosteroids (e.g. triamcinolone). Thus viewed from a still further aspect the disclosure provides a substance such as a local anaesthetic or corticosteroid for use in a method for treating or preventing headache, rhinitis, rhinosinusitis, Frey syndrome or hypersecretion of tears/lacrimation comprising injecting said substance in close proximity to the sphenopalatine ganglion or otic ganglion wherein an injection device comprising said substance is brought into close proximity to the sphenopalatine ganglion or otic ganglion by inserting said injection device into the patient transnasally or infrazygomatically and the substance injected in close proximity to the SPG or OG.

Various example procedures using the device described above are set out below.

Example 1

A female patient with refractory hemicrania continua was treated via injection of Botox around the SPG. Due to an occipital neurostimulator MRI was contraindicated and identification of SPG on MRI was not possible. Preoperatively the calculated position of the SPG was marked on a CT scan with 1 mm slides based on the knowledge of average distances from landmarks as stated above. On the navigation planning system a preplanned puncture site and trajectory was made. On the symptomatic side a navigable needle guide was advanced through the sphenopalatine foramen and towards the SPG. The needle was passed through the guide and the tip of the needle was confirmed to be 1 mm from the SPG by the navigation system while 75 IU botulinum toxin type A was injected.

Over a period of two months prior to the treatment the patient had an average headache intensity of 8.1 (scale 1-10) and normally experienced from one to four headache attacks daily. From 4 to 10 weeks after the treatment the patient had not a single attack during the whole period and the average headache intensity was 6.3. The patient did not experience any complication during 4 months follow-up.

Example 2

A female patient with refractory chronic cluster headache was treated via injection of lidocaine around the OG. Preoperatively the calculated position of the SPG was marked on a CT scan with 1 mm slides. On the navigation planning system a preplanned puncture site and trajectory was made. On the symptomatic side a navigable needle guide was advanced through the maxillary ostium and the backwall of the maxillary sinus, and then at the lateral aspects of the lateral pterygoid plate to the OG. 5 ml of lidocaine 20 mg/ml was injected. The patient had a short relief of the headache as expected using short-acting local anaesthetic.

The invention claimed is:

1. A method of treating or preventing a medical condition comprising injecting a neuroinhibitory substance in close proximity to the sphenopalatine ganglion ("SPG") or otic ganglion ("OG"), wherein an injection device comprising said neuroinhibitory substance is brought into close proximity to the sphenopalatine ganglion or otic ganglion by inserting said injection device into the patient transnasally or infrazygomatically, and the neuroinhibitory substance is injected in close proximity to the SPG or OG,
  wherein the injection device defines a straight line from skin/mucosa penetration to a point where the neuroinhibitory substance release occurs close to a location of the SPG or OG, and wherein the location is identified prior to insertion of the device.

2. The method of claim 1, wherein the neuroinhibitory substance is injected in close proximity to the SPG.

3. The method of claim 1, wherein the neuroinhibitory substance is injected in close proximity to the OG.

4. The method of claim 2, wherein the SPG is targeted infrazygomatically.

5. The method of claim 1, wherein the substance is injected within 5 mm of the SPG or OG.

6. The method of claim 1, wherein the neuroinhibitory substance is botulinum toxin, tetanus neurotoxin, staphylococcal alpha-toxin or acylpolyamine toxin.

7. The method of claim 1, wherein said injection device comprises:
   an end piece for insertion into body tissues at a distal end thereof, the end piece including a rigid lumen for holding an instrument and guiding the instrument to the distal end of the end piece; and
   a body section supporting the lumen and being rigidly connected thereto, the body section including a navigation array for guidance of the device using a surgical navigation system and/or including an anchor point for a standard navigation array.

8. The method of claim 7, wherein the distal end of the end piece comprises a tip for piercing body tissues, the tip having a tapered profile narrowing toward a point.

9. The method of claim 8, wherein the tip is adapted to bend the instrument away from a longitudinal axis of the end piece as the instrument is pushed through the lumen and out of the tip.

10. The method of claim 7, wherein the end piece comprises a scale or other marking to show the depth of insertion of the end piece into body tissues.

11. The method of claim 7, wherein the lumen is rigid enough to permit placement of a tip of the end piece with millimeter accuracy without deformation as the lumen penetrates body tissues and whilst being subject to bending moments that might arise as it is maneuvered along the selected approach toward a target site.

12. The method of claim 11, wherein the lumen has a rigidity sufficient to enable the tip to be placed with millimeter accuracy at the sphenopalatine ganglion ("SPG") when targeted via a infrazygomatic approach.

13. The method of claim 7, wherein the lumen has a rigidity sufficient to limit deflection of a needle as it advances toward the SPG along the lateral approach to a maximum of 2 mm per 10 cm of length of the lumen.

14. The method of claim 7, wherein the navigation array is rigidly connected to the body section, the array comprising a plurality of optical or electromagnetic markers located in plane with one another and at known locations relative to the end piece.

15. The method of claim 7, wherein the injection device comprises a proximal piece for holding a proximal end of the instrument, the proximal piece being positioned at a proximal end of the end piece and being connected to the end piece either directly or via the body section.

16. The method of claim 15, wherein the proximal piece comprises one or more clamp(s) for attachment of the instrument, the clamp or clamps being for fixing the instrument in place relative to the end piece and the distal end thereof.

17. The method of claim 15, wherein the proximal piece comprises moveable parts for connection to the instrument and for movement with the instrument as it moves relative to the end piece.

18. The method of claim 14, wherein the navigation array is held in a track on the body section that permits slidable movement relative to the body section, and wherein the navigation array is rigidly connected to the instrument via a coupling between the proximal piece and the navigation array.

19. The method of claim 7, wherein the end piece is for receiving and guiding a needle.

20. The method of claim 7, wherein the lumen is sized to receive a needle of 25 G or smaller.

21. The method of claim 7, wherein the instrument comprises a needle, the needle including a needle tip having a slightly rounded end and openings on each side of the tip rather than at the tip end.

22. The method of claim 21, wherein the injection device comprises a proximal piece for holding a proximal end of the instrument, the proximal piece being positioned at a proximal end of the end piece and being connected to the end piece either directly or via the body section, and wherein a vessel is attached to the needle at the body section or the proximal piece.

23. The method of claim 22, wherein the injection device comprises a locking mechanism to lock the proximal piece and a injection mechanism to aspirate and then inject a substance from the vessel.

24. The method of claim 1 wherein the device is guided to a position in close proximity to the SPG or OG using surgical navigation.

25. The method of claim 1, wherein the neuroinhibitory substance is injected into the patent to treat or prevent a headache.

26. The method of claim 1, wherein the neuroinhibitory substance is injected into the patent to treat or prevent rhinitis, rhinosinusitis, Frey syndrome or hypersecretion of tears.

* * * * *